(12) United States Patent
Koennecke

(10) Patent No.: US 9,510,749 B2
(45) Date of Patent: Dec. 6, 2016

(54) CHIN-REST AND BASE FOLDING ARRANGEMENT FOR AN OPHTHALMIC INSTRUMENT

(71) Applicant: Gregory Koennecke, Hobart (AU)

(72) Inventor: Gregory Koennecke, Hobart (AU)

(73) Assignee: Vision Instruments Pty Ltd (AU)

( * ) Notice: Subject to any disclaimer, the term of this patent is extended or adjusted under 35 U.S.C. 154(b) by 0 days.

(21) Appl. No.: 14/443,427

(22) PCT Filed: Dec. 12, 2013

(86) PCT No.: PCT/AU2013/001461
§ 371 (c)(1),
(2) Date: May 18, 2015

(87) PCT Pub. No.: WO2014/089631
PCT Pub. Date: Jun. 19, 2014

(65) Prior Publication Data
US 2015/0282702 A1    Oct. 8, 2015

(30) Foreign Application Priority Data
Dec. 12, 2012  (AU) ................ 2012905422

(51) Int. Cl.
*A61B 3/00* (2006.01)
*A61B 3/10* (2006.01)
*A61B 3/02* (2006.01)

(52) U.S. Cl.
CPC ................. *A61B 3/0083* (2013.01)

(58) Field of Classification Search
CPC ......... A61B 3/1015; A61B 3/18; A61B 3/103; A61B 3/08; A61B 3/14; A61B 3/113; A61B 3/1225; A61B 3/024; A61B 3/032
USPC ........................ 351/245, 246, 200, 201, 203, 205–206,351/210, 221–224
See application file for complete search history.

(56) References Cited

U.S. PATENT DOCUMENTS

| | | | |
|---|---|---|---|
| 2,132,520 A * | 10/1938 | Taylor | A61B 3/113 346/107.1 |
| 3,944,342 A * | 3/1976 | Martinez | A61B 3/14 351/206 |
| 6,286,960 B1 | 9/2001 | Tomita | |
| 7,594,728 B2 | 9/2009 | Seal et al. | |
| 2007/0171372 A1* | 7/2007 | Seal et al. | A61B 3/005 351/245 |

* cited by examiner

*Primary Examiner* — Dawayne A Pinkney
(74) *Attorney, Agent, or Firm* — Renner Kenner Greive Bobak Taylor & Weber

(57) ABSTRACT

A base support arm is provided for an ophthalmic instrument with a moveable optics head. The base support arm is configured so that the support arm must be deployed to stabilize the instrument before the instrument head can be moved sideways in a manner that could otherwise destabilize the instrument. In addition, an angled chin-rest assembly pivot axis is provided that moves the chin-rest assembly from a compactly folded shape into a position that is suitable for supporting the patient's head. The support arm is linked to the chin-rest assembly pivot by a linkage or other mechanism so that movement of the support arm also unfolds the chin-rest assembly and ensures that the chin-rest assembly cannot be unfolded without deploying the support arm.

15 Claims, 4 Drawing Sheets

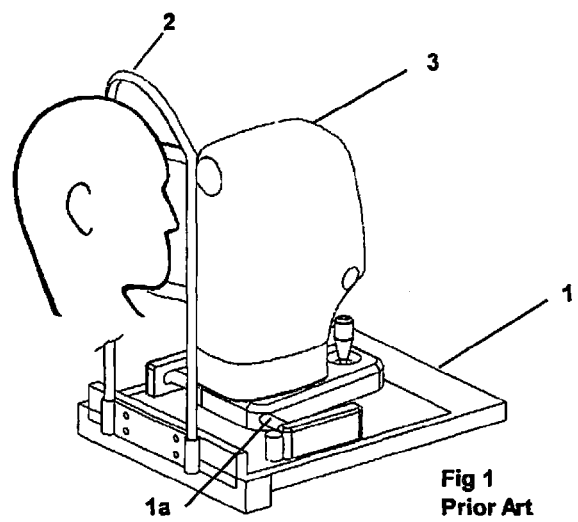
Fig 1
Prior Art
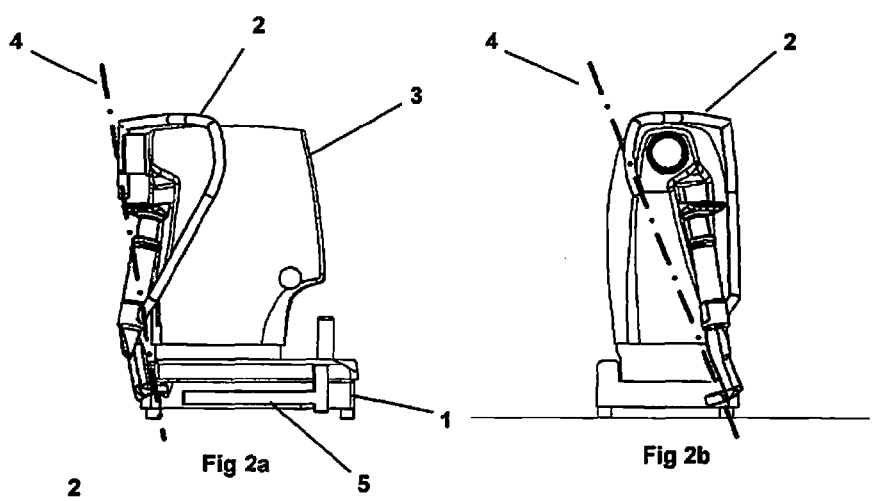
Fig 2a
Fig 2b
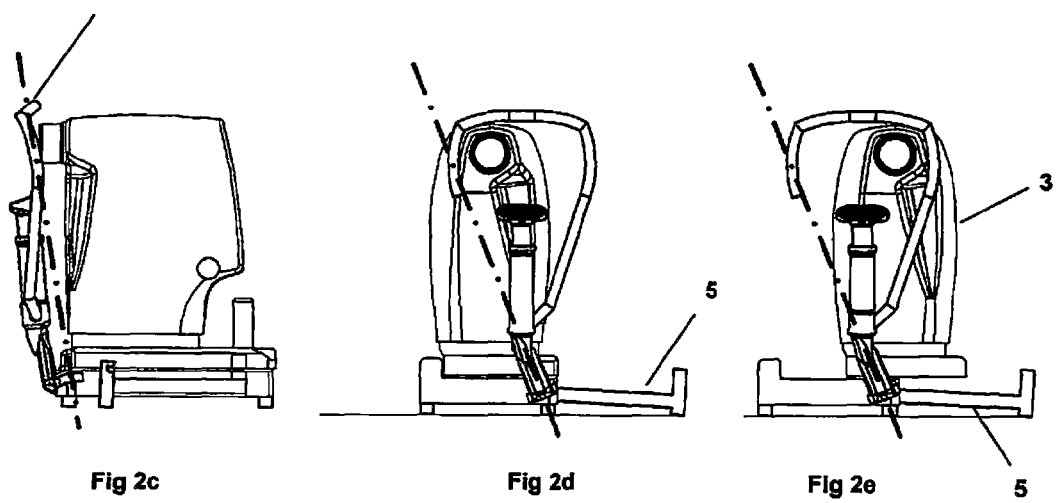
Fig 2c
Fig 2d
Fig 2e

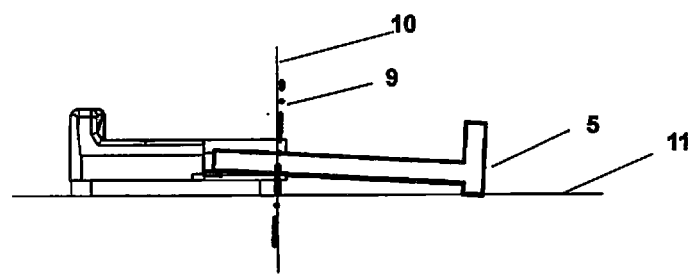
Fig 6a
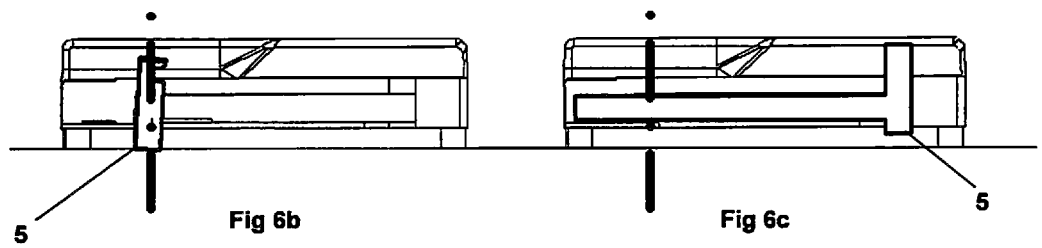
Fig 6b  Fig 6c
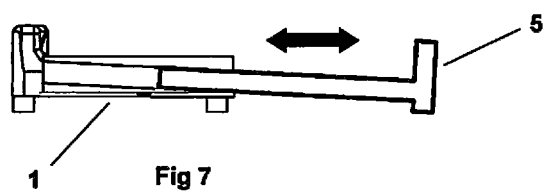
Fig 7
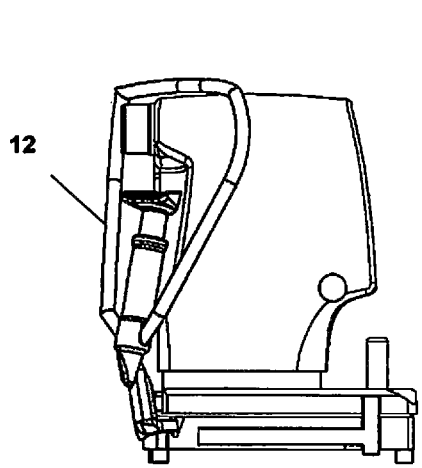 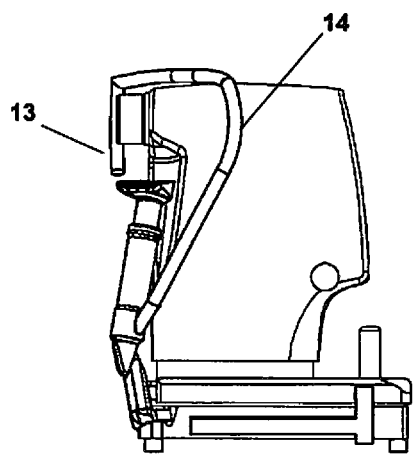
Fig 8a  Fig 8b

CHIN-REST AND BASE FOLDING ARRANGEMENT FOR AN OPHTHALMIC INSTRUMENT

CROSS-REFERENCE TO RELATED APPLICATIONS

This application is a National Phase filing of International Application No. PCT/AU2013/001461, filed Dec. 12, 2013, which claims the benefit of Australian Patent Application No. 2012905422, filed Dec. 12, 2012, both of which are incorporated herein by reference in their entirety.

TECHNICAL FIELD

This invention relates to a mechanical arrangement and method for folding the base and chin-rest assemblies of an ophthalmic instrument

BACKGROUND ART

Ophthalmic instruments often include a chin and forehead rest to stabilise a subject's head during an examination or procedure on the subject eye. Typical ophthalmic instruments that are mounted on a base and have a chin-rest assembly include retinal or fundus cameras, slit lamps and tonometers.

It is sometimes required that the ophthalmic instrument is transported to a different area to provide a service. When transporting an ophthalmic instrument which has a chin-rest and base that do not fold, a case large enough to fit the instrument is required. The size of the instrument is typically defined by the necessary size of the base to allow movement of the moveable instrument optics head sideways to view both subject eyes whilst remaining stable, and a protruding chin-rest to support the subject's head while sitting upright with the instrument base resting on a conventional table. As a result the transport case for the non-folding ophthalmic instrument is typically too large to be carried on commercial airline flights as standard check-in luggage, and certainly too large to carry on-board as personal luggage.

Some manufacturers have addressed this problem by allowing the chin-rest and base to be detached from the instrument so that the various components can be packaged more compactly for transport. Although effective, this is not convenient for the user as disassembly and packing of separate components is required. The width of the base and chinrest may still be larger than necessary as the base width has to be sufficient to prevent the instrument falling over when the moveable optics head is moved sideways. Removable or folding supports may be provided to maintain the stability of the instrument in this situation, but there is a risk that the instrument may fall over if the support is not properly in place when the moveable optics head is moved sideways.

It is desirable that an arrangement for folding the base and chin-rest of an ophthalmic instrument without separation be provided that allows the instrument dimensions to be reduced to a size that is suitable for carrying on-board commercial airline flights or for transport in a padded carry case that is small enough to be checked in as standard baggage. A reduction in size of the ophthalmic instrument also improves portability for general transport and manual carrying. It is also desirable that the folding arrangement does not require tools, and is such that the system does not have to be unfolded or assembled in a particular order to avoid an unstable configuration existing.

A previous design by this inventor comprised a chinrest assembly that slid upwards and rotated into normal working position and a support arm that folded out horizontally to provide the necessary stability. This system was effective, but the folded instrument was less compact than required, the folding action was complex and not entirely intuitive. After much experimentation a different arrangement was devised that is the subject of this patent application.

SUMMARY OF THE INVENTION

This invention provides an arrangement for folding the base and chin-rest of an ophthalmic instrument without separation, to allow the instrument dimensions to be reduced to a size more convenient for transport.

DISCLOSURE OF THE INVENTION

According to the present invention, a base support arm is provided that is configured so that the support arm must be deployed to stabilise the instrument before the instrument head can be moved sideways in a manner that could otherwise destabilise the instrument. In addition an angled chin-rest assembly pivot axis is provided that moves the chin-rest assembly from a compactly folded shape into a position that is suitable for supporting the subject's head. The support arm is linked to the chin-rest assembly pivot by a linkage or other mechanism so that movement of the support arm also unfolds the chin-rest assembly and ensures that the chin-rest assembly cannot be unfolded without deploying the support arm.

BRIEF DESCRIPTION OF THE DRAWINGS

In the drawings:

FIG. 1 shows a conventional prior art ophthalmic instrument with an outline indicating the position of head of the subject whose eye is being examined.

FIG. 2a shows a side view representation of an arrangement for a folding ophthalmic instrument that is the subject of this patent, shown in a folded position.

FIG. 2b shows a front view representation of the arrangement of FIG. 2a.

FIG. 2c shows a side view representation of an arrangement for a folding ophthalmic instrument that is the subject of this patent shown in an open position.

FIG. 2d shows a front view representation of the arrangement of FIG. 2c.

FIG. 2e shows a front view representation as in FIG. 2d, but shown with the optics head moved sideways relative to FIG. 2d

FIG. 6a shows a front view of the base, showing how the pivot axis of the folding support arm is angled away from the vertical, so that the folding support arm moves away from the table on folding.

FIG. 6b shows a side view of FIG. 6a, showing the support arm in the open position.

FIG. 6c shows a side view as in FIG. 6b, showing the support arm in the closed position.

FIG. 7 shows an alternative arrangement where the support arm slides linearly out of the base rather than rotating around a pivot axis.

FIG. 8a is a side view showing a chin-rest assembly with an additional section 12 that can be avoided to provide a chin-rest assembly with a shape so as to minimize the size of the instrument in a folded configuration.

FIG. 8b shows removal of section 12 of FIG. 8a to shows an asymmetrically shaped forehead rest designed to protrude a minimum amount when folded for transport, while forming a carry handle when in the folded position.

MODE FOR CARRYING OUT THE INVENTION

Figure 3A:
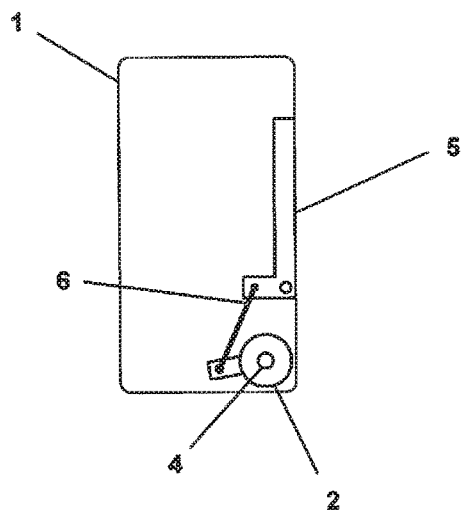
FIG. 3a shows a bar linkage system designed to cause the chin-rest assembly to fold as the support arm is folded, with the support arm shown folded to a position in the base.

Referring now to the drawings,

FIG. 1 shows how the size of a conventional ophthalmic instrument is defined by the height and position of the chinrest assembly 2 that supports the subject's head, and width of the base 1 necessary to ensure that the instrument remains stable as the moveable optics head 3 is moved sideways to allow examination of both of the subject's eyes.

FIG. 2 shows an arrangement for a folding ophthalmic instrument that is the subject of this patent. The chin-rest assembly 2 rotates around an inclined axis 4 from the folded position shown in FIGS. 2a and 2b to the open position shown in FIGS. 2c and 2d. A support arm 5 is unfolded at the same time as the chin-rest assembly, to ensure that the stability of the instrument is maintained as the optics head 3 is moved sideways as indicated in FIG. 2e.

The pivot point for the inclined axis 4 is near one corner of the base 1 and the pivot axis passes through this pivot point and a point near to the opposite top corner of the chinrest assembly. Because of the angle of the pivot axis, the top of the chin-rest assembly moves rearwards and downwards as the chin-rest assembly is folded back closely against the moveable optics head 3.

In a further embodiment of this invention, the chin-rest assembly 2 is linked to the folding support arm 5 such that moving the support arm causes the chin-rest assembly to move to the operational or stored position. This linkage may be achieved by a rigid bar linkage 6 with suitable end bearings, a bowden cable 7 or other cable or chord or chain connection.

Figure 5A:
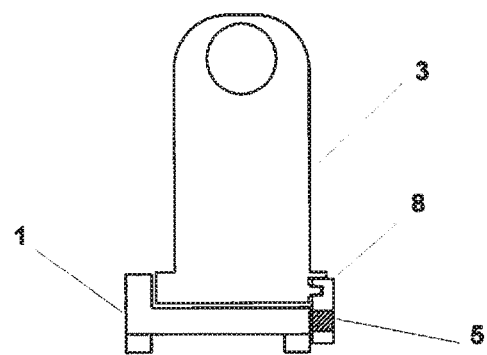
FIG. 5a shows a protrusion 8 on the folding support arm 5 that locks the moveable optics head sideways and downwards when the folding support arm is in the folded position and ensures that the support arm must be unfolded before the moveable instrument head can be moved sideways, the folding support arm being shown in the folded position.
Figure 5B:
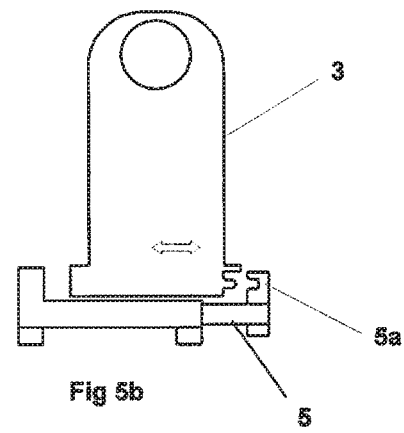
FIG. 5b shows the protrusion of FIG. 5a, but shown with the folding support arm in an unfolded position.

A further feature if the invention is the protrusion 8 at the end of the folding support arm 5 shown in FIG. 5, that ensures that the folding arm is always pushed towards the unfolded position as the moveable optics head 3 is moved sideways as depicted in FIG. 5b. The protrusion 8 may also lock into the moveable optics head 3 as indicated in FIG. 5a when the folding support arm is in the folded position, to ensure that the optics head 3 cannot be lifted away from the base 1 or moved laterally when the support arm is in the folded position.

It is preferable that the pivot axis 9 of the folding support arm 5 is angled to the vertical 10 as indicated in FIG. 6a. This angled pivot ensures that the end of the folding support arm 5 is lifted clear of the table surface 11 as the support arm is moved to from the open position depicted in FIG. 6b to the closed position depicted in FIG. 6c.

Figure 3B:
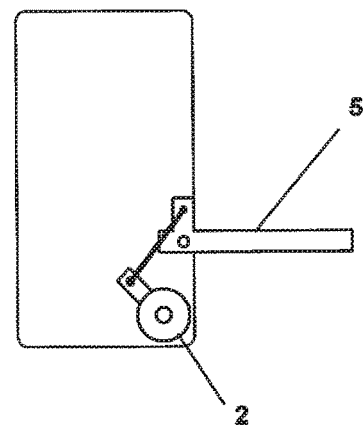
FIG. 3b shows a bar linkage system of FIG. 3a but with the support arm folded to a position outside the base.
Figure 4:
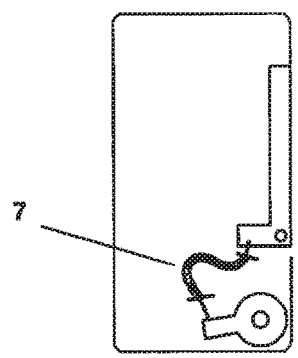
FIG. 4 shows an alternative linkage comprising a bowden cable linking the chin-rest assembly to the support arm.

As an alternative embodiment of this invention, the support arm 5 may slide out linearly from within the base 1, as depicted in FIG. 7. The support arm may be linked to the folding chinrest assembly by a linkage or bowden cable as proposed for the pivoting version of the invention as discussed above and depicted in FIGS. 3 and 4.

It is desirable that the chin-rest assembly be shaped so as to minimise the size of the instrument in the folded condition. To achieve this requirement the chin-rest assembly may be asymmetric by deleting section 12 in FIG. 8a, and by bending the unsupported end of the chinrest assembly 13 backwards as depicted in FIG. 8b to minimise the forward and sideways protrusion of the chin-rest assembly when in the folded position.

The curved section 14 of the folded chin-rest assembly in FIG. 8b may be near the plane of the centre of mass of the folded instrument and so may act as a carry handle for the ophthalmic instrument when in the folded position.

Figure 9:
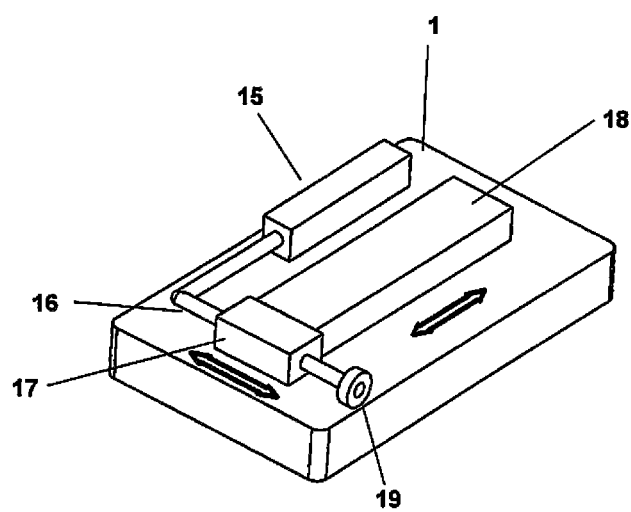
FIG. 9 shows a support shaft bearing arrangement.

With reference to FIGS. 1 and 2, it can be seen that the folding concept depicted in FIG. 2 that is the subject of this invention does not allow the long slide shaft 1a supported at both ends to guide the head 3 sideways and forward/back as conventionally used in ophthalmic instruments and shown in FIG. 1. An alternative narrower slide mechanism was developed as depicted in FIG. 9, with slide bearing 15 mounted to the base 1, where an L shaped shaft arrangement 16 slides in the slide bearing 15, and this L shaped shaft in turn slides in a slide bearing 17 that supports the head mounting plate 18. The end of the shaft arrangement 16 is supported by rolling bearing 19. This arrangement provides restraint for the head mounting plate 18 such that the head mounting plate (and so the head 3) can only move in the forward or sideways direction (as indicated by arrows in FIG. 9), as required to align the optics head 3 with the subject's eye.

In a further embodiment of this invention, the ophthalmic instrument may be provided with a powered actuator to move the optics head vertically, and a micro-switch, or a magnetic sensor, or an optical sensor or other sensor that indicates when the support arm is in the out position stabilising the instrument and the linked chin-rest assembly is in the out position, so that it is safe for the powered vertical axis actuator to drive the moveable head vertically upwards. With such a powered vertical axis actuator it is desirable that the actuator automatically drives the optics head of the ophthalmic instrument downwards when the instrument is shut down, so that the chin-rest assembly can thereafter be folded into the most compact volume.

The invention claimed is:

1. An arrangement of a base and folding chin-rest for an ophthalmic instrument including:

an ophthalmic instrument that includes a base, a moveable ophthalmic instrument head and a chin-rest assembly;

a chin-rest assembly that includes a forehead rest and a chin-rest to stabilize the subject's head, and a means to rotate the chin-rest assembly to fold closely against the moveable ophthalmic instrument head without needing to detach the base, the moveable ophthalmic instrument head, or the chin-rest assembly, and wherein the chin-rest assembly rotates around one front corner of the base of the instrument and the projection of the chin-rest assembly rotation axis passes through a point near the top of the chin-rest assembly above the other front corner of the instrument such that the chin-rest assembly rotates backwards and downwards as it is rotated into the transport position; and a support arm which fits within or compactly against the base for transport, then folds or slides out to stabilize the ophthalmic instrument when the moveable instrument head is moved sideways in use.

2. A folding arrangement of claim 1 where the support arm is linked to the chin-rest assembly by a linking device such that the chin-rest assembly is rotated to the transport position when the support arm is moved to its transport position.

3. A folding arrangement of claim 2 where the linking device is a bar with pivot bearings at each end.

4. A folding arrangement of claim 2 where the linking device is a bowden cable that acts in tension and compression.

5. A folding arrangement of claim 2 where the linking device is simple chord or cable or chain that acts in tension.

6. A folding arrangement of claim 2 where the support arm has a protrusion that prevents the moveable instrument head from moving through its full range until the support arm is unfolded to the point where it provides the extra support necessary to provide adequate stability to the instrument.

7. A folding arrangement of claim 6 where the protrusion locks the moveable instrument head in the transport position when the support arm is locked in the transport position.

8. A folding arrangement of claim 1 where the support arm rotates around a pivot axis that is not vertical, so that the end of the support arm moves upwards away from the table as it is rotated into the transport position.

9. A folding arrangement of claim 1 where the support arm slides linearly into the base of the instrument for transport.

10. A folding arrangement of claim 9 where the support arm slides upwards away from the table as it is slid into the transport position.

11. A folding arrangement of claim 1 that includes a chin-rest assembly structure that is asymmetric in shape so that the structure protrudes a minimum amount when folded for transport.

12. A folding arrangement of claim 1 that includes a chin-rest assembly structure that is shaped so as to form a carry handle when in the folded position.

13. A folding arrangement of claim 1 where the moveable ophthalmic instrument head is supported on an L shaped shaft arrangement that slides in one slide bearing that is fixed to the instrument base and a second slide bearing that is fixed to the moveable ophthalmic instrument head.

14. A folding arrangement of claim 1 with a powered vertical axis actuator and a microswitch, or a magnetic sensor, or an optical sensor or other sensor that indicates when the support arm is in the out position stabilizing the instrument and the chin-rest assembly is in the out position, so that it is safe for the powered vertical axis actuator to drive the moveable head vertically upwards.

15. A folding arrangement of claim 12 with a powered vertical axis actuator that automatically drives the optics head of the ophthalmic instrument downwards when the instrument is shut down, so that the chin-rest assembly can thereafter be folded into the most compact volume.

\* \* \* \* \*